United States Patent [19]

Manoury et al.

[11] Patent Number: 4,891,376
[45] Date of Patent: Jan. 2, 1990

[54] 1-((2-PYRIMIDINYL)AMINOALKYL)PIPERI-DINES, THEIR PREPARATION AND THEIR APPLICATION IN THERAPY

[75] Inventors: Philippe Manoury, Verrieres le Buisson; Alfred Saarmets, Sucy en Brie, both of France

[73] Assignee: Synthelabo, Paris, France

[21] Appl. No.: 242,430

[22] Filed: Sep. 8, 1988

[30] Foreign Application Priority Data

Sep. 9, 1987 [FR] France .................. 87 12502

[51] Int. Cl.$^4$ .................. A61K 31/505; C07D 409/14
[52] U.S. Cl. .................... 514/272; 544/321; 544/331; 546/202; 546/203; 546/204
[58] Field of Search ............... 544/321, 331; 514/272

[56] References Cited
FOREIGN PATENT DOCUMENTS
0037713 10/1981 European Pat. Off. .

Primary Examiner—Glennon H. Hollrah
Assistant Examiner—James H. Turnipseed
Attorney, Agent, or Firm—Fleit, Jacobson, Cohn, Price, Holman & Stern

[57] ABSTRACT

A compound which is a pyrimidinylamino derivative of piperidine of formula (I)

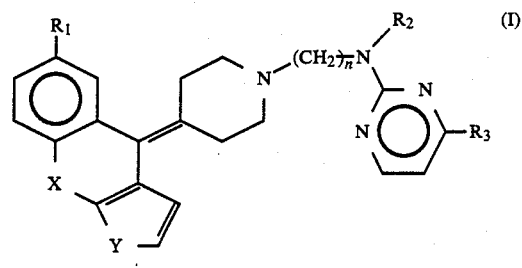

in which:
X is a $(CH_2)_2$, $CH=CH$ or $CH_2-CO$ group;
Y is a $CH=CH$ gruop or sulphur;
n is 2, 3 or 4;
$R_1$ is hydrogen or a halogen;
$R_2$ is hydrogen or a ($C_{1-4}$) alkyl group; and
$R_3$ is hydrogen or a hydroxy group;
or a pharmaceutically acceptable acid addition salt thereof.

7 Claims, No Drawings

1-((2-PYRIMIDINYL)AMINOALKYL)PIPERIDINES, THEIR PREPARATION AND THEIR APPLICATION IN THERAPY

The present invention relates to pyrimidinylamino derivatives of piperidine, to their preparation, to pharmaceutical compositions containing them and to their application in therapy.

The present invention provides a compound which is a pyrimidinylamino derivative of piperidine of formula (I) given in Appendix 1 in which:
X is a $(CH_2)_2$, $CH=CH$ or $CH_2-CO$ group;
Y is a $CH=CH$ group or sulphur;
n is 2, 3 or 4;
$R_1$ is hydrogen or a halogen, for example fluorine or chlorine;
$R_2$ is hydrogen or a ($C_{1-4}$) alkyl group, for example a methyl group; and
$R_3$ is hydrogen or a hydroxy group;
or a pharmaceutically acceptable acid addition salt thereof.

The compound may, for example, be in the form of a maleate, dihydrochloride or oxalate salt.

According to the invention, the compounds of formula (I) may be prepared according to the reaction scheme given in Appendix 1.

The present invention relates to pyrimidinylamino derivatives of piperidine, to their preparation, to pharmaceutical compositions containing them and to their application in therapy.

The present invention provides a compound which is a pyrimidinylamino derivative of piperidine of formula (I) given in Appendix 1 in which:
X is a $(CH_2)_2$, $CH=CH$ or $CH_2-CO$ group;
Y is a $CH=CH$ group or sulphur;
n is 2, 3 or 4;
$R_1$ is hydrogen or a halogen, for example fluorine or chlorine;
$R_2$ is hydrogen or a ($C_{1-4}$) alkyl group; and
$R_3$ is hydrogen or a hydroxy group;
or a pharmaceutically acceptable acid addition salt thereof.

The compound may, for example, be in the form of a maleate dihydrochloride or oxalate salt.

According to the invention, the compounds of formula (I) may be prepared according to the reaction scheme given in Appendix 1.

The present invention also provides a process for preparing a compound as defined above which comprises reacting a compound of formula (V) or (VI):

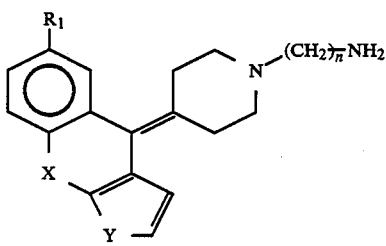

or

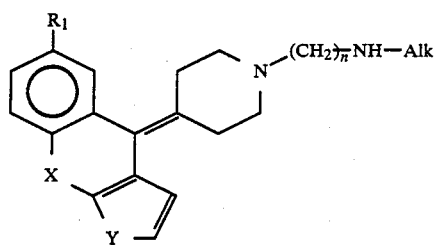

in which X, Y, n and $R_1$ are as defined in claim 1 and Alk is a $C_{1-4}$ alkyl group with a compound of formula (VII):

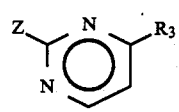

in which $R_3$ is as defined in claim 1 in a solvent, for example methyl isobutyl ketone or toluene, at a temperature of from 80° to 130° C. and, if desired, forming a pharmaceutically acceptable acid addition salt of the compound of formula (I) thus obtained.

The compound of formula (V) may be prepared by reacting a compound of formula (III):

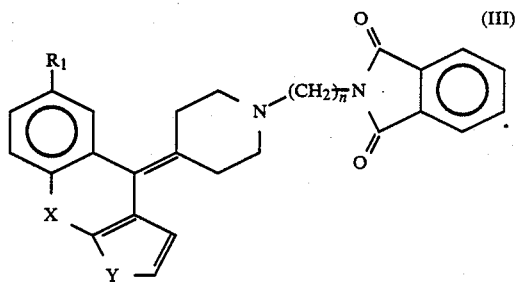

in which X, Y, n and $R_1$ are as defined above with hydrazine.

The compound of formula (VI) may be prepared by hydrolyzing a compound of formula (IV):

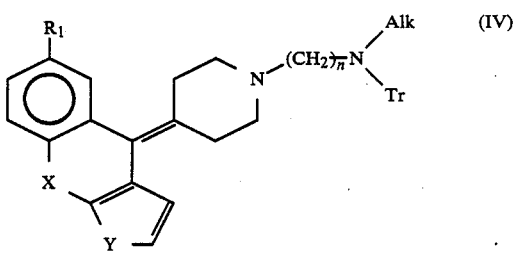

in which X, Y, n, $R_1$ and Alk are as defined above and T is a trityl group.

The compound of formula (III) or (IV) may be prepared by reacting a compound of formula (II):

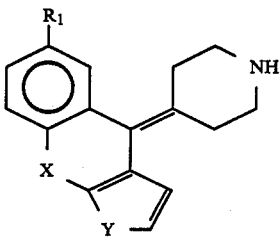

in which X, Y and R₁ are as defined above with a compound of formula:

$$R(CH_2)_n—Z$$

in which n is as defined above, R is a phthalamido or N(Alk)Tr group, in which Tr is as defined above, Alk is a $C_{1-4}$ alkyl group, for example a methyl group, and Z is a labile group, for example iodine, in a solvent, such as methyl isobutyl ketone, at a temperature of from 80° to 130° C.

In order to form a compound of formula (I) wherein $R_2$ is methyl, the compound of formula (V) may also be reduced with trifluoroacetic anhydride of formula $(F_3CO)_2O$ to form a compound of formula (VIII):

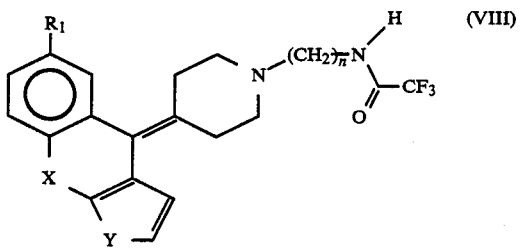

in which X, Y, n and $R_1$ are as defined above.

The compound of formula (VIII) may then be reacted with methyl iodide to form the compound of formula (VI).

The starting compounds of formula (II) are either described in the literature or obtained from compounds described in the literature, for example according to the reaction scheme depicted in Appendix 2.

Compounds of formula Z—(CH₂)ₙ—N(Alk)(trityl) are described by J. D. Billimoria and K. O. Lewis, J. Chem. Soc. Chem. Comm. 1404 (1968).

The Examples which follow further illustrate the present invention.

The IR and NMR spectra confirm the structure of the compounds.

EXAMPLE 1

4-(10,11-Dihydro-3-fluoro-5H-dibenzo[a,d]cyclohepten-5-ylidene)-1-{2-[N-methyl-N-(2-pyrimidinyl)amino]ethyl}pipeidine.

1.1.
10,11-Dihydro-3-fluoro-5-(1-methyl-4-piperidyl)-5H-dibenzo[a,d]cyclohepten-5-ol Tetrahydrofuran (THF) is introduced into a 4 l reactor containing finely ground magnesium (40 g; 1.65 mol) until the magnesium is just covered, and a crystal of iodine is introduced, followed by pure 4-chloro-1-methylpiperidine (2-3 ml). When a brisk reaction occurs, stirring is begun, and 4-chloro-1-methylpiperidine, dissolved in THF (210 g; 1.57 mol; 200 ml of THF) is added at a rate such that refluxing of the THF is maintained. When the addition is complete, 500 ml of THF are added and refluxing is continued for 2 hours. The reaction mixture is then cooled to 5° C. A solution of 10,11-dihydro-3-fluoro-5H-dibenzo[a,d]cyclohepten-5-one (175 g; 0.775 mol; 750 ml of THF) (British Patent Application 2,132,618) is then added dropwise, after which the mixture is allowed to return slowly to room temperatue and stirring is continued at room temperature for 2 hours. The reactor is then placed in a cooling mixture (−10° C.) and the magnesium derivative is hydrolysed by the slow addition of saturated aqueous ammonium chloride solution (190 ml); the mixture is stirred for 1 hour at room temperature, filtered and washed with THF, and the filtrate is evaporated to dryness. The oil obtained is taken up with methylene chloride, the mixture is washed with water, dried and evaporated, the oil is redissolved in ether (500 ml) and ethereal hydrogen chloride (500 ml; 4 mol/l) is added dropwise, the mixture is stirred for 1 h at room temperature and the precipitated product is filtered off, washed with ether, then with water and then again with ether. The hydrochloride thereby obtained is added to aqueous sodium hydroxide solution (1,000 ml; 2.5 mol/l). The base is extracted with methylene chloride, the extract is washed with water, dried and evaporated and the product is crystallized in hexane. The product is recrystallized in isopropanol. M.p. 175° C.

1.2.
10,11-Dihydro-3-fluoro-5-(1-cyano-4-piperidyl)-5H-dibenzo[a,d]cyclohepten-5-ol The product obtained in the preceding stage (83 g; 0.26 mol) is added in small portions, using a powder funnel, to a solution of cyanogen bromide (30 g; 0.28 mol) in rigorously dry benzene (1,000 ml); the reaction mixture is then stirred for 10 h at room temperature. The benzene is evaporated off and the crude product obtained (m.p. 250° C.) is used without further treatment in the following stage.

1.3
4-(10,11-Dihydro-3-fluoro-5H-dibenzo[a,d]cyclohepten-5-ylidene)piperidine After the above crude cyanamide (86 g; 0.256 mol) has been suspended in aqueous acid actic solution (2 l of acetic acid, 1.5 l of water), 260 ml of concentrated hydrochloric acid are added dropwise and the mixture is then heated to the refluxing temperature for 10 h (passage into solution at 80° C.). The mixture is concentrated to half the volume under reduced pressure, placed in the refrigerator for 2 hours, filtered, washed with water and ether and dried. The product is obtained in the form of a white hydrochloride. M.p. 340° C. Base; M.p. 105° C.

1.4.
4-(10,11-Dihydro-3-fluoro-5H-dibenzo[a,d]cyclohepten-5-ylidene)-1-[2-(N-methylamino)ethyl]piperidine A mixture of 4-(10,11-dihydro-3-fluoro-5H-dibenzo[a,d]cyclohepten-5-ylidene)piperidine (5 g; 0.017 mol) and 2-[N-methyl-N-(triphenylmethyl)amino]ethyl iodide (7.3 g; 0.017 mol) in 30 ml of methyl isobutyl ketone (MiBK) is heated to the refluxing temperature. Potassium carbonate (4.7 g; 0.034 mol) is added in a single portion at this temperature, and the mixture is then heated to the refluxing temperature under an argon atmosphere for 10 h. The mixture is cooled, filtered and evaporated to dryness. The residual oil is then taken up with methylene chloride and the mixture is washed with water and with saline, dried over magnesium sulphate and then evaporated to dryness. 100 ml of 1N hydrochloric acid are added to the oil obtained, and the mixture is then stirred for 5 hours at room temperature. The tritylmethanol is separated off by filtration, the mother liquors are neutralized with 2N aqueous sodium hydroxide, the product is extracted using methylene chloride and the extract is dried over magnesium sulphate and evaporated. The oil obtained is used without further purification in the following stage.

1.5
4-(10,11-Dihydro-3-fluoro-5H-dibenzo[a,d]cyclohepten-5-ylidene)-1-{2-[N-methyl-N-(2-pyrimidinyl)amino]ethyl}piperidine A mixture of the compound obtained in the preceding stage (4.7 g; 0.0135 mol) and 2-chloropyrimidine (1.7 g; 0.0148 mol) in 25 ml of MiBK is heated to the refluxing temperature. Sodium hydrogen carbonate (2.5 g; 0.03 mol) is added in a single portion at this temperature, and the mixture is heated to the refluxing temperature for 8 hours under an argon atmosphre. The mixture is filtered, the inorganic insoluble material is washed with methylene chloride and the mixture is evaporated to dryness. The residual oil is chromatographed on Merck silica 60, eluting with a methylene chloride/acetone (50:50, v/v) mixture. The solvents are evaporated off from the fraction which contain the product. A stoichiometric quantity of maleic acid, in alcoholic solution, is added to the solution of the crude base in ethyl acetate. After standing for one night, the maleate of the desired product is filtered off.

The crystallized product has a 1.5 mol of maleic acid per mol of base. M.p. 135° C.

EXAMPLE 2

4-(3-Fluoro-5H-dibenzo[a,d]cyclohepten-5-ylidene)-1-{2-[N-methyl-N-(2-pyrimidinyl)amino]ethyl}piperidine.

2.1
3-Fluoro-5-(1-methyl-4-piperidyl)-5H-dibenzo[a,d]cyclohepten-5-ol

This compound is prepared from 3-fluoro-5H-dibenzo[a, d]cyclohepten-5-one (British Patent Application 2,132,618) according to the method described in Example 1.1. M.p. 300° C. (hydrochloride).

2.2. 3-Fluoro-5-(1-cyano-4-piperidyl)-5H-dibenzo[a, b]cyclohepten-5-ol

Starting with the above compound 2.1., this compound is obtained using the method of synthesis of Example 1.2 M.p. 280° C.

2.3
4-(3-Fluoro-5H-dibenzo[a,d]cyclohepten-5-ylidene)-piperidine

The above cyanamide 2.2. is hydrolysed under the conditions described in Example 1.3. M.p.>300° C. (hydrochloride); m.p. 161° C. (base).

2.4.
4-(3-Fluoro-5H-dibenzo[a,d]cyclohepten-5-ylidene)-1-[2-(N-methylamino)ethyl]piperidine This compound is prepared from 4-(3-fluoro-5H-dibenzo[a,d]cyclohepten-5-ylidene)piperidine (2.5 g; 0.0085 mol) according to the procedure used for the synthesis of the compound described in Example 1.4. It is used without further treatment in the following stage.

2.5 4-(3-Fluoro-5H-dibenzo[a,d]cyclohepten-5-ylidene)-1-{2-(N-methyl-N-(2-pyrimidinyl)amino]ethyl}piperidine Starting with the above compound 2.4 (2 g; 0.0057 mol) and 2-chloropyrimidine (0.7 g; 0.061 mol), according to the alkylation method described for the derivative of Example 1.5., the desired compound is obtained in base form. A maleate is prepared. M.p. 184° C.

EXAMPLE 3

4-(5H-Dibenzo[a,d]cyclohepten-5-ylidene)-1-{2-[N-(2-pyrimidinyl)amino]ethyl}piperidine 3.1.
4-(5H-Dibenzo[a,d]cyclohepten-5-ylidene)-1-[2-(1,3-dioxo-2-isoindolinyl)ethyl]piperidine A mixture of norcyproheptadine [Englehardt et al., J. Med. Chem. 8, 829 (1965)] (10 g; 0.036 mol) and 2-(2-bromoethyl)-1,3-dioxyisoindole (9.9g; 0.039 mol) in methyl isobutyl ketone (200 ml) is brought to the refluxing tempertuure. After 10 min of stirring at the refluxing temperature, potassium carbonate (11 g; 0.08 mol) is introduced in a single portion. Refluxing is continued for 8 h, the mixture is filtered and evaporated and the crude product obtained is purified by recrytallization in methanol. The expected product is isolated in this manner in base form. M.p. 190° C.

3.2.
4-(5H-Dibenzo[a,d]cyclohepten-5-ylidene)-1-(2-aminoethyl)piperidine

A methanolic solution of hydrazine (250 ml; 1.4 mol/l) is added dropwise to a suspension of the above compound 3.1. (26 g; 0.059 mol) in methanol (250 ml), and the mixture is then stirred at room temperature for 8 hours. It is evaporated to dryness (coevaporation with three times 250 ml of methanol), the mixture thereby obtained is then taken up with methylene chloride, the resulting mixture is filtered, the mother liquors are washed with 2N aqueous sodium hydroxide and saline, dried and evaporated, and the product is crystallized in pentane. M.p. 102° C. (base).

3.3.
4-(5H-Dibenzo[a,d]cyclohepten-5-ylidene)-1-{2-[N-(2-pyrimidinyl)amino]ethyl}piperidine A mixture of the compound 3.2. (1.3 g; 0.004 mol) and 2-chloropyrimidine (0.5 g; 0.004 mol) is brought to the refluxing temperature in methyl isobutyl ketone (10 ml), and sodium bicarbonate (0.4 g; 0.005 mol) is then added 10 min later. Refluxing is maintained for 20 hours. The mixture is filtered, the solvent is evaporated off and the residual oil is chromatographed on silica (Merck $SiO_2$ 40, eluant: methylene chloride/methanol, 9:1 v/v). After evaporation, the crude base is obtained, the maleate of which is prepared and recrystallized in ethyl acetate. M.p. 198° C.

EXAMPLE 4

4-(5H-Dibenzo[a,d]cyclohepten-5-ylidene)-1-{2-[N-methyl-N-(2-pyrimidinyl)amino]ethyl}piperidine and its maleate

4.1.

4-(5H-Dibenzo[a,d]cyclohepten-5-ylidene)-1-[2-(N-methylamino)ethyl]piperdine

A mixture of norcyproheptadine (6.8 g; 0.025 mol) and 2-[N-methyl-N-(triphenylmethyl)amino]ethyl iodide (10.16 g; 0.025 mol) in 50 ml of MiBK is brought to the refluxing temperature. Potassium carbonate (6.8 g; 0.050 mol) is then added in a single portion, and the mixture is heated to the refluxing temperature for 10 hours under an argon atmosphere. After it has been allowed to cool, it is filtered and the filtrate is evaporated to dryness. The oil obtained is dissolved in methanol containing oxalic acid (3 g; 0.033 mol).The solution is evaporated to dryness, the residue is taken up with aqueous acetic acid (100 ml; 90%), and the mixture is brought to reflux for 30 min, concentrated to half the volume and left in the refrigerator. The crystallized oxalate is filtered off and dried. M.p. 205° C. (decomposition).

4.2.

4-(5H-Dibenzo[a,d]cyclohepten-5-ylidene)-1-{2-[N-(2-pyrimidinyl)amino]ethyl}piperidine and its maleate A mixture of the compound obtained in the preceding stage 4.1. (2.1 g; 0.006 mol) and 2-chloropyrimidine (0.8 g; 0.007 mol) in 10 ml of MiBK is brought to the refluxing temperature. After 10 min of refluxing, sodium bicarbonate (1 g; 0.0012 mol) is added and refluxing is continued for 4 h. The mixture is filtered and evaporated to dryness, the residue is taken up with methylene chloride and the resulting mixture is washed with water and saline, dried over magnesium sulphate and evaporated. The oil obtained is dissolved in isopropanol, and 0.7 g of maleic acid dissolved in 10 ml of methanol is then added. The mixture is concentrated to 2/3 and left to stand for 8 h. The crystallized product is filtered off, washed with ether and dried at 40° C. at reduced pressure. The maleate is obtained. M.p. 179° C.

EXAMPLE 5

4-(5H-Dibenzo[a,d]cyclohepten-5-ylidene)-1-{3-[N-methyl-N-(2-pyrimidinyl)amino]propyl}piperidine

5.1.

4-(5H-Dibenzo[a,d]cyclohepten-5-ylidene)-1-[3-(1,3-dioxo-2-isoindolinyl)propyl]piperidine Starting with norcyproheptadine and 2-(3-bromopropyl)-1,3-dioxoisoindole and employing the method of synthesis described in Example 3.1., the compound is prepared. M.p. 266° C. (hydrochloride).

5.2.

4-(5H-Dibenzo[a,d]cyclohepten-5-ylidene)-1-(3-aminopropyl)piperidine

This product is prepared from the above compound 5.1. according to the procedure used for the synthesis of the derivative described in Example 3.2. M.p. 95° C. (base).

5.3

4-(5H-Dibenzo[a,d]cyclohepten-5-ylidene)-1-[3-(N-trifluoroacetylamino)propyl]piperidine Trifluoroacetic anhydride (4.5 ml; 0.032 mol) is added dropwise, using a syringe, to a solution of the compound 5.2 (10 g; 0.03 mol) in 50 ml of chloroform containing 0.1 ml of concentrated sulphuric acid and cooled to 0° C. When the addition is complete, the mixture is stirred for 10 min at 0° C., 250 ml of water are then added followed by sodium bicarbonate in small portions (20 g; 0.24 mol), and the organic phase is separated off after settling has occurred, washed with saline and then dried. After evaporation to dryness, the oil obtained is crystallized in n-butyl ether. M.p. 106° C.

5.4.

4-(5H-Dibenzo[a,d]cyclohepten-5-ylidene)-1-[3-(N-methylamino)propyl]piperidine

Ethereal hydrogen chloride is added to the product obtained above in Example 5.3. (11 g; 0.026 mol) dissolved in 200 ml of methanol, and the mixture is then evaporated to dryness. Acetone is added to the hydrochloride obtained, the mixture is heated to the refluxing temperature and a solution of methyl iodide in acetone (6 g; 0.042 mol in 50 ml) is then added dropwise. After 20 min of refluxing, powdered potassium hydroxide (3.5 g; 0.062 mol) is added cautiously, and the mixture is heated for a further 30 min at the refluxing temperature and then evaporated to dryness. The residue is taken up in 200 ml of water and the mixture is then heated to the refluxing temperature for 30 mi, left to cool and extracted with methylene chloride. The methylene chloride is evaporated off and the residue is chromatographed on silica (Merck $SiO_2$ 40, eluant: methanol/concentrated ammonia solution mixture, 90:10 v/v). After evaporation of the solvents, the oil is taken up with methylene chloride and the mixture is washed with water, dried and evaporated. The desired product is obtained, and used without further treatment in the following stage.

5.5.

4-(5H-Dibenzo[a,d]cyclohepten-5-ylidene)-1-{3-[N-methyl-N-(2-pyrimidinyl)amino]propyl}piperidine.

This compound is prepared from compound 5.4. and 2-chloropyrimidine according to the method of synthesis described in Example 4.2. M.p. 129° C. (base).

TABLE

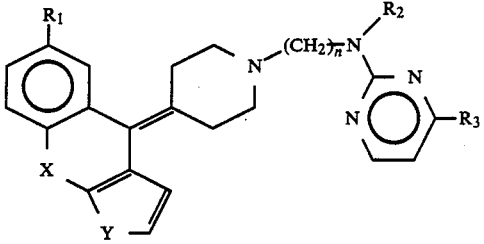

| Compound | n | R₁ | X | Y | R₂ | R₃ | Salt | M.p. (°C.) |
|---|---|---|---|---|---|---|---|---|
| 1 | 2 | H | CH=CH | CH=CH | H | H | maleate | 198 |
| 2 | 2 | H | CH=CH | CH=CH | CH₃ | H | maleate | 179 |
| 3 | 2 | H | CH=CH | CH=CH | H | OH | dihydrochloride | 252 |
| 4 | 2 | H | CH=CH | CH=CH | CH₃ | OH | hydrochloride | 200 |
| 5 | 2 | H | CH₂—CH₂ | CH=CH | CH₃ | H | maleate | 134 |
| 6 | 2 | F | CH=CH | CH=CH | CH₃ | H | maleate | 184 |
| 7 | 2 | F | CH₂—CH₂ | CH=CH | H | H | maleate | 149 |
| 8 | 2 | F | CH₂—CH₂ | CH=CH | CH₃ | H | maleate | 143 |
| 9 | 2 | F | CH₂—CH₂ | CH=CH | CH₃ | OH | maleate | 136 |
| 10 | 2 | Cl | CH₂—CH₂ | CH=CH | H | H | maleate | 154 |
| 11 | 2 | Cl | CH₂—CH₂ | CH=CH | CH₃ | H | maleate | 165 |
| 12 | 2 | Cl | CH₂—CH₂ | CH=CH | CH₃ | OH | maleate | 138 |
| 13 | 3 | H | CH=CH | CH=CH | H | H | base | 95 |
| 14 | 3 | H | CH=CH | CH=CH | CH₃ | H | base | 129 |
| 15 | 2 | H | CH₂—CO | S | CH₃ | H | oxalate | 192 |
| 16 | 2 | H | CH₂—CH₂ | S | CH₃ | H | oxalate | 205 |
| 17 | 2 | H | CH₂—CO | S | CH₃ | OH | oxalate | 140 (dec) |
| 18 | 3 | Cl | CH₂—CH₂ | CH=CH | CH₃ | H | maleate | 147 |
| 19 | 4 | Cl | CH₂—CH₂ | CH=CH | CH₃ | H | maleate | 151 |

The compounds of the invention possess an antiserotonin activity (in respect of the 5HT2 type receptors).

This activity was demonstrated "in vitro" by the displacement of ligands bound specifically to serotoninergic receptors (SBS binding test), and "in vivo" by antagonism of the effects of serotonin at peripheral level (OES test) and at central level (AHT test).

SBS Test: the compounds of the invention were subjected to a test of displacement of the binding of spiroperidol to the serotoninergic (5-HT2) receptors of rat cerebral cortex.

For this test, rat brains are removed and the cortex is dissected out and homogenized at 0° C. in 10 volumes of a mixture containing, per liter, 50 millimoles of Tris/HCl buffer at pH 7.4, 120 millimoles of sodium chloride and 5 millimoles of potassium chloride. The homogeneous mixture is centrifuged at 40,000×g for 10 min, and the pellet is then recovered twice, washed by suspending it in the same buffer mixture, homogenized again and centrifuged. Lastly, the final pellet is diluted in the same buffer mixture in the proportion of 100 mg of wet tissue for 1 ml of buffer.

The tissue is then subjected to a prior 10-min incubation at 37° C. in the presence of 10 micromoles/l of pargyline, and then to a 20-min incubation at 37° C. in the presence of [³H]isoproperidol (specific activity: 25.6 Ci per millimole) at a concentration of 0.3 nanomole/l and test compound at concentrations ranging from 0.0001 to 100 micromoles/l.

1 ml aliquots are removed and filtered under vacuum, and the filters are washed twice with 5 ml of cold buffer and dried. The radioactivity is measured in toluene in the presence of 5 g/l of 2,5-diphenyloxazole (PPO) and 0.1 g/l of 1,4-bis(5-phenyl-2-oxazolyl)benzene (POPOP).

To assess the activity of the compounds, the curve is plotted for the percentage inhibition of the specific binding of [³H]spiroperidol as a function of the concentration of displacing drug. The IC₅₀ concentration, the concentration which inhibits 50% of the specific binding, is determined grphically.

The specific binding is defined as the binding displaced by 100 micromoles/l of 5-HT.

The IC₅₀ concentration of the compounds of the invention lie for the most part between 1 and 50 nanomoles/l.

OES Test: the antiserotoninergic activity of the compounds of the invention was also demonstrated by their effect on serotonin-induced oedema in rats, according to the method described by Maling et al., J. Pharmacol. Exp. Therap., 191 (2), 300–310 (1974).

The animals are CD strain male rats (Ch. River, France) weighing 120 to 150 g, fasted for 18 h and distributed in randomized sets.

The compounds, dissolved or suspended in Tween 80 at a concentration of 1%, are administered orally in the proportion of 0.5 ml for 100 g of bodyweight, 1 h before the sub-plantar injection of 1 μg of serotonin (dissolved in sterile physiological saline, in a volume of 0.1 ml) into one of the hind legs. The volume of oedema is measured 1 h after the injection of serotonin by means of an Ugo Basile mercury plethysmometer. The AD₄₀ (dose which decreases by 40% the volume of the oedema, relative to the control animals9 is determined graphically.

The AD₄₀ of the compounds of the invention, determined orally, is between 0.1 and 2 mg/kg.

AHT Test: the antiserotoninergic activity of the compounds was studied in respect to their effect on the antagonism of "head-twitches" induced by L-5-hydroxytryptophan (L-5-HTP) in mice, according to the method described by Corne et al., Br. J. Pharmacol., 20, 106–120 (1962).

The mice (CD1 males, Charles River France; 18–22 g of bodyweight) receive the test products at increasing doses, or the solvent, intraperitoneally or orally, simultaneously (i.p. administration) or sixty minutes before (oral administration) a subcutaneous injection of L-5-HTP at a dose of 250 mg/kg. Forty-five minutes after this injection of 5-HTP, the number of twitches is counted, for each mouse, for one minute.

For each treatment, the mean number of twitches, as well as the percentage variation relative to the control batch, are calculated.

From the dose-response curve, the $AD_{50}$ (50% active dose or dose which decreases by 50% the mean number of twiches relative to the control animals) is determined by the graphic method of Miller and Tainter (Proc. Soc. Exp. Biol. Med., (1944), 57, 261).

The $AD_{50}$ values of the compounds of the invention lie between 0.05 and 2 mg/kg intraperitoneally and between 0.1 and 4 mg/kg orally.

The daily dosage can range from 5 to 200 mg.

The compounds of the invention may be administered orally or parenterally, in combinatin with any suitable excipient. Accordingly the present invention provides a pharmaceutical composition comprising a compound as define above and a pharmaceutically acceptable excipient.

The compounds of the invention may be useful for the treatment of migraine, anxiety, depression, obesity, inflammation, asthma, allergies, vascular or gastrointestinal spasms, hypertension and platelet aggregation, and as antiemetics.

Some compounds also possess antihistaminic activity.

The present invention provides a compound of formula (I) or a pharmaceutically acceptable acid addition salt thereof for use in a method of treatment of the human or animal body by therapy.

The present invention additionally provides a compound of formula (I) or a pharmaceutically acceptable acid addition salt thereof for use in the treatment of migraine, anxiety, depression, obesity, inflammation, asthma, an allergy, vascular or gastrointestinal spasms, hypertension or platelet aggregation or for use as an antiemetic or antihistaminic.

The present invention further provides use of a compound of formula (I) or a pharmaceutically acceptable acid addition salt thereof in the manufacture of a medicament for the treatment of migraine, anxiety, depression, obesity, inflammation, asthma, an allergy, vascular or gastrointestinal spasms, hypertension or platelet aggregation or for use as an antiemetic or antihistaminic.

Appendix 1

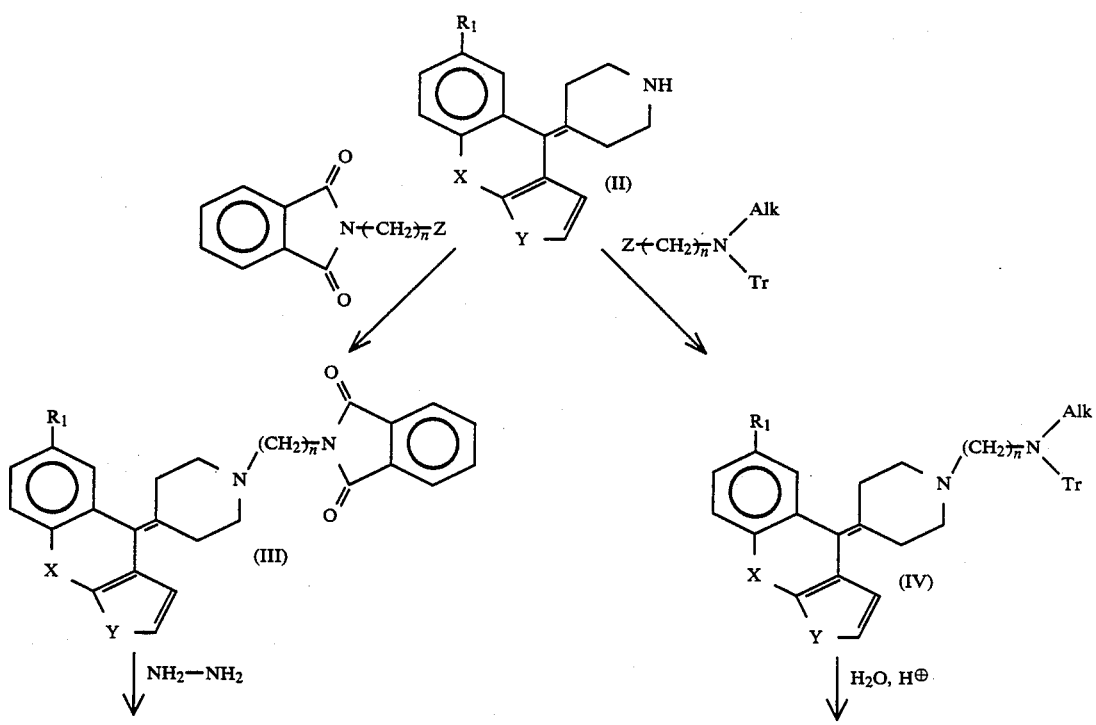

-continued
Appendix 1
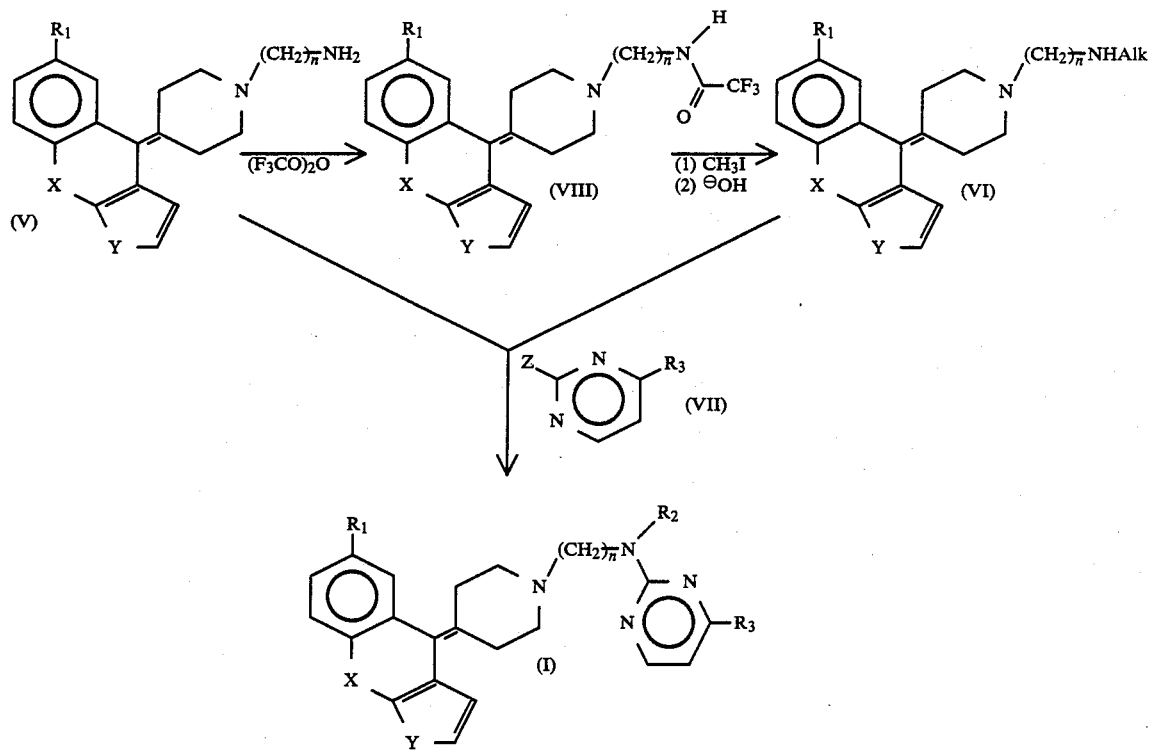
Appendix 2
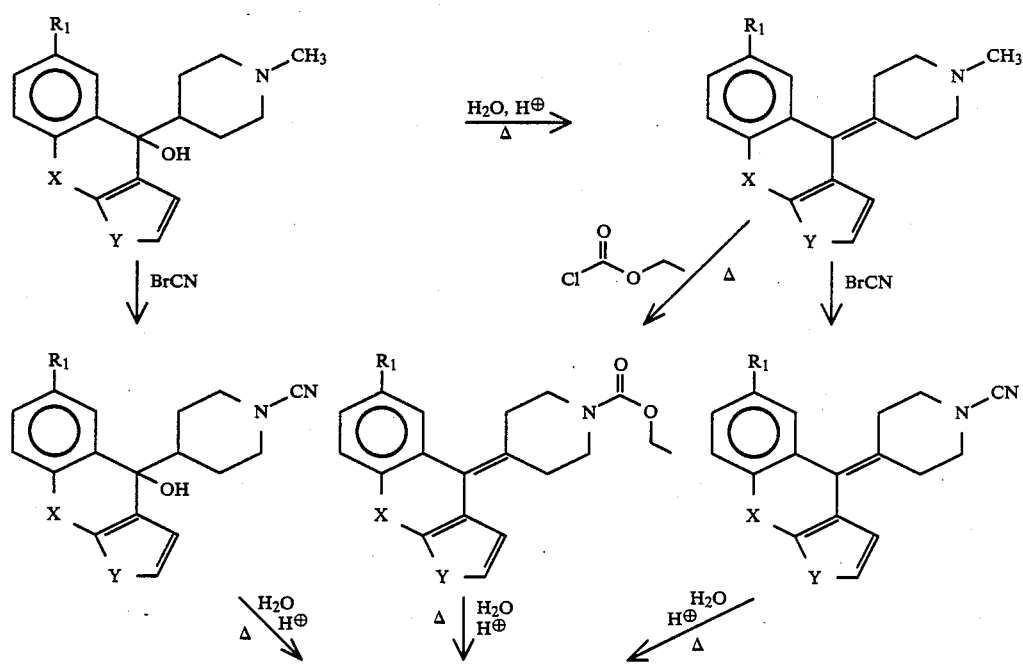

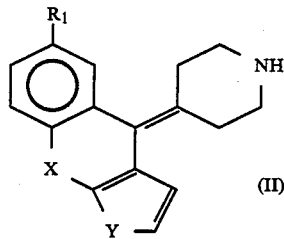

(II)

We claim:

1. A compound which is a pyrimidinylamino derivative of piperidine of formula (I)

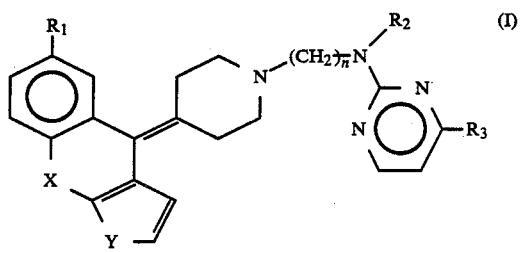

in which:
X ix a (CH₂)₂, CH=CH or CH₂—CO group;
Y is a CH=CH group or sulphur;
n is 2, 3 or 4;
R₁ is hydrogen or a halogen;
R₂ is hydrogen or a (C₁₋₄) alkyl group; and
R₃ is hydrogen or a hydroxy group;
or a pharmaceutically acceptable acid addition salt thereof.

2. A compound according to claim 1 wherein n is 2.

3. A compound according to claim 1 wherein R₁ is hydrogen, chlorine or fluorine.

4. A compound according to claim 1 wherein R₂ is hydrogen or a methyl group.

5. A compound according to claim 1 which is in the form of a maleate, dihydrochloride or oxalate salt.

6. A pharmaceutical composition comprising a pharmaceutically effective amount of a compound as defined in claim 1 and a pharmaceutically acceptable excipient.

7. A method for the treatment of migraine which comprises administering to a subject suffering therefrom or liable to suffer therefrom an effective amount of a compound as defined in claim 1.

* * * * *